United States Patent
Citron et al.

(10) Patent No.: US 6,444,108 B1
(45) Date of Patent: Sep. 3, 2002

(54) PROCESS FOR ISOLATION OF DICARBOXYLIC ACIDS AND HYDROXYCARBOXLIC ACIDS

(75) Inventors: Joel David Citron; Michael Robert Samuels, both of Wilmington, DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/591,479

(22) Filed: Jun. 9, 2000

Related U.S. Application Data

(60) Continuation of application No. 09/186,988, filed on Nov. 5, 1998, now abandoned, which is a division of application No. 08/832,739, filed on Apr. 4, 1997, now Pat. No. 5,928,485.
(60) Provisional application No. 60/014,998, filed on Apr. 8, 1996.

(51) Int. Cl.⁷ ............................................... B01D 61/44
(52) U.S. Cl. ...................... 204/541; 204/544; 204/530; 204/531
(58) Field of Search ................................ 204/541, 544, 204/530, 531

(56) References Cited

U.S. PATENT DOCUMENTS 4,093,528 A  6/1978  Wynkoop et al.
5,772,013 A  * 6/1998  Kunz et al. ............... 204/541
5,928,485 A  * 7/1999  Citron et al. ............. 204/541

FOREIGN PATENT DOCUMENTS

GB  1198087  7/1970
JP  40-11492  6/1965
JP  64-9954  7/1987

* cited by examiner

Primary Examiner—Arun S. Phasge

(57) ABSTRACT

A first process involves the partial electrodialysis of a dialkali metal salt of an aromatic hydroxycarboxylic acid or a dicarboxylic acid to produce the approximate monoalkali metal salt and the alkali metal hydroxide. The monoalkali metal salt is then treated with an acid such as a bisulfate to recover the aromatic hydroxycarboxylic acid or dicarboxylic acid. The resulting inorganic salt such as sodium sulfate may then be electrolyzed to sodium bisulfate and NaOH. A second process involves the electrodialysis at elevated temperatures of a (di)alkali metal salt of p-hydroxybenzoic acid produce free p-hydroxybenzoic acid and the alkali metal hydroxide. These are efficient and economical methods for recovering the acid and alkali metal hydroxide values, as well as the parent organic compound, from these dialkali metal salts.

10 Claims, 2 Drawing Sheets

PROCESS FOR ISOLATION OF DICARBOXYLIC ACIDS AND HYDROXYCARBOXLIC ACIDS

This application claims the priority benefit of U.S. Provisional Application No. 60/014,998, filed Apr. 8, 1996. This application is a continuation of application Ser. No. 09/186,988 filed Nov. 5, 1998, now abandoned, which is a division of application Ser. No. 08/832,739 filed Apr. 4, 1997 now U.S. Pat. No. 5,928,485.

FIELD OF THE INVENTION

This invention concerns a process for the isolation of dicarboxylic acids and aromatic hydroxycarboxylic acids from their alkali metal salts by partially electrodialyzing these salts and then reacting the salt of the dicarboxylic acid or hydroxycarboxylic acid with a Bronsted acid. This invention also concerns a process for the isolation of p-hydroxybenzoic acid from its mono- or dialkali metal salts by electrodialyzing these salts. Alkali metals and their hydroxides may be completely and economically recycled in the process.

BACKGROUND OF THE INVENTION

Aromatic hydroxycarboxylic acids and dicarboxylic acids are important items of commerce. For instance o-hydroxybenzoic acid (salicylic acid) is used as a chemical intermediate, for instance to make aspirin, while p-hydroxybenzoic acid (PHBA) is used to make parabens and is also used as a monomer in making polyesters, while dicarboxylic acids are important as monomers. Traditionally aromatic hydroxycarboxylic acids are manufactured using the Kolbe-Schmitt reaction, which is a reaction of an alkali metal salt of an aromatic hydroxy compound with carbon dioxide, usually under elevated temperature and pressure. The Kolbe-Schmitt reaction has been a standard procedure for the preparation of aromatic hydroxy acids for over 100 years, see for instance A. S. Lindsey, et al., Chem. Rev., vol. 57, p. 583–620 (1957) incorporated by reference herein. However, this process is complex and difficult to run, involving several manufacturing steps, which adds to the cost of the final product. Since the initial product of the carboxylation reaction is a dialkali metal salt of the aromatic hydroxycarboxylic acid, substantial cost is usually incurred for the use of compounds such as NaOH or KOH which are subsequently discarded (as sodium or potassium salts), since the free aromatic hydroxycarboxylic acid (or dicarboxylic acid) is usually isolated by reacting the dialkali metal salt with a strong acid. It is hence desirable to develop an improved Kolbe-Schmitt process for the manufacture of these compounds. Dicarboxylic acids are also sometimes available as their dialkali metal salts, and it is often desirable to convert these to the dicarboxylic acids themselves, and generate an alkali from the alkali metals present in the salts.

It is known that the salts of diacids or aromatic hydroxycarboxylic acids can be electrodialyzed to form the free dicarboxylic acid or aromatic hydroxycarboxylic acid and the alkali metal hydroxide. However, when one tries to completely electrodialyze these compounds to these final products, as one approaches complete electrolysis, the voltage increases and the current efficiency decreases rapidly and the process may become uneconomic. Therefore, it would be desirable to have another economical method for isolating the free aromatic hydroxycarboxylic acid or dicarboxylic acid from its dialkali metal salt, while at the same time being able to recycle the alkali metals in the process in an economical fashion.

Japanese Patent Application 40-11492 describes the electrodialysis of an alkali metal salt of terephthalic acid to terephthalic acid and an alkali metal hydroxide.

Japanese Patent Application 64-9954 describes the electrodialysis of an alkali metal salt of hydroxybenzoic acid.

None of the above references describes a partial electrodialysis followed by a treatment with a strong acid to effect isolation of a dicarboxylic acid or an aromatic hydroxycarboxylic acid.

Electrodialysis of salts of organic compounds is in general known, and generally requires only relatively simple equipment. However, if one attempts to electrodialyze an aqueous solution of the mono- or dipotassium salt of PHBA, one finds that before free PHBA is obtained, the voltage required to effect electrolysis greatly increases and the electrolysis essentially stops (see Comparative Example 1). However it has now been found that if this electrodialysis is done at elevated temperatures, good results can be obtained.

SUMMARY OF THE INVENTION

A first process of this invention for the preparation of a dicarboxylic acid or an aromatic hydroxycarboxylic acid from its dialkali metal salt, comprises, (a) electrodialyzing a compound of the formula $(OR^1CO_2)M_2$ or $[R^2(CO_2)_2]M_2$ to produce a compound of the formula $(OR^1CO_2)H_yM_{2-y}$ or $[R^2(CO_2)_2]H_yM_{2-y}$ and MOH; and (b) reacting $(OR^1CO_2)H_yM_{2-y}$ or $[R^2(CO_2)_2]H_yM_{2-y}$ with:

a Bronsted acid of the formula $M_qH_{s-q}X$ whose pKa in water is about 4 or less; or an aqueous solution of a Bronsted acid of the formula HT whose pKa in water is about 4 or less, said aqueous solution optionally containing at least 5 mole percent of HT or MT;

to form $(OR^1CO_2)H_2$ or $[R^2(CO_2)_2]H_2$ and a T or X salt of M, and wherein:

T is monovalent anion;

$R^1$ is arylene or substituted arylene $R^2$ is hydrocarbylene or substituted hydrocarbylene;

M is an alkali metal cation;

s is the valence of X;

y is about 0.10 to about 1.90;

q is about 0.10 to about (s−0.10); and

X is a polyvalent anion.

A second process of this invention for the preparation of p-hydroxybenzoic acid from its dialkali metal salt, comprises, electrodialyzing an aqueous solution of a first compound of the formula $(OR^1CO_2)H_tM_{2-t}$ to produce a second compound of the formula $(OR^1CO_2)H_yM_{2-y}$ and MOH, wherein:

$R^1$ is p-phenylene;

t is zero to about 1.50;

M is an alkali metal cation; and y is about 1.95 to 2.00;

and provided that when y or t is about 1.0 or more, said electrodialysis is carried out at a temperature of about 75° C. or more.

DETAILED DESCRIPTION OF THE INVENTION

Figure 1:
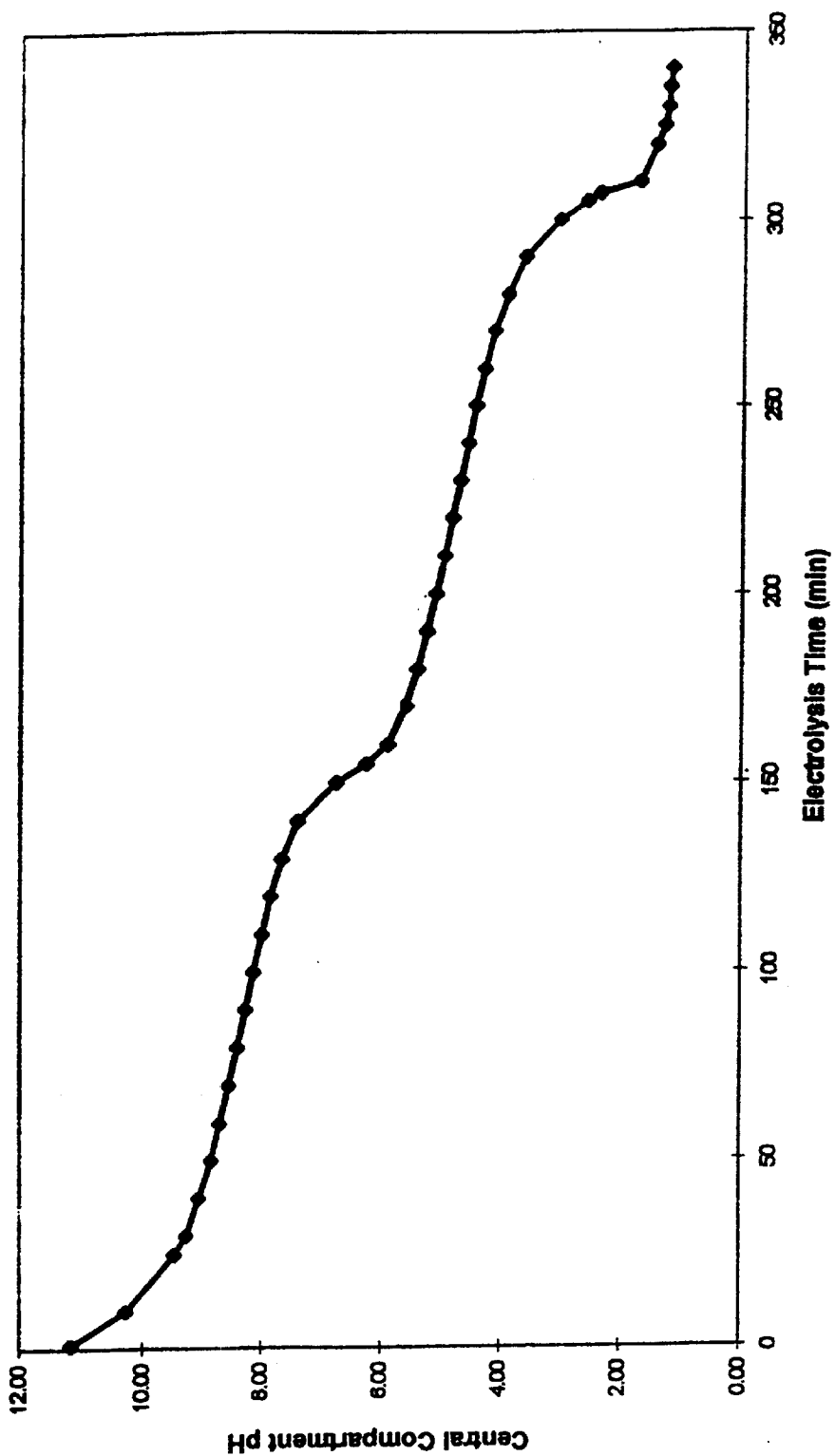
FIG. 1 is a graph showing data from Example 1 of electrolysis time vs. pH of the solution in the central compartment of the electrodialysis cell.

The product of the first process of the invention is an aromatic hydroxycarboxylic acid or a dicarboxylic acid or a partial alkali metal salt thereof. By an aromatic hydroxycarboxylic acid is meant a compound that contains at least one aromatic carbocyclic ring, and at least one hydroxyl group and one carboxyl group, both of which are attached to a carbon atom of an aromatic carbocyclic ring. This compound may contain one or more aromatic rings, and if more than one such ring is present they may be fused, as in naphthalene, connected by a covalent bond, as in biphenyl, or by a divalent group, as in diphenyl ether. There may also be inert groups attached to the aromatic ring(s), such as one or more alkyl groups. Compounds which may produced by this process include p-hydroxybenzoic acid, o-hydroxybenzoic acid, 2-hydroxy-3-methylbenzoic acid, 2-hydroxy-5-methylbenzoic acid, 2,4-dihydroxybenzoic acid, and a hydroxynapthoic acid. Preferred products are p-hydroxybenzoic acid, 6-hydroxy-2-napthoic acid, and o-hydroxybenzoic acid.

The product of the first process may also be a dicarboxylic acid. It is preferred that the product is an aromatic dicarboxylic acid. By an aromatic dicarboxylic acid is meant a compound that contains at least one aromatic carbocyclic ring, and also contains two carboxyl groups attached to carbon atoms of one or more aromatic carbocyclic ring. This compound may contain one or more aromatic rings, and if more than one such ring is present they may be fused, as in naphthalene, connected by a covalent bond, as in biphenyl, or by a divalent group, as in diphenyl ether or diphenylmethane. There may also be inert groups attached to the aromatic ring(s), such as one or more alkyl groups and/or halogens. Preferred product aromatic dicarboxylic acids are isophthalic acid, terephthalic acid, 4,4'-bibenzoic acid, and 2,6-naphthalene dicarboxylic acid.

By arylene herein is meant a radical with two free valencies to carbon atoms of one or two aromatic rings. By hydrocarbylene herein is meant a divalent radical containing carbon and hydrogen. By "substituted" herein is meant one or more substitutents that don't interfere with the reactions described herein. Suitable substitutents include alkyl and halogen.

The starting material for this first process is the corresponding dialkali metal salt of an aromatic hydroxycarboxylic acid or dicarboxylic acid or its partially acidified form of the formula $(OR^1CO_2)H_zM_{2-z}$ or $[R^2(CO_2)_2]H_zM_{2-z}$, wherein z is less than 1, more preferably 0 to about 0.5 and especially preferably less than about 0.1. This compound is then electrolyzed so that the value of z is increased to y, y normally being greater than z. Usually there will be essentially only one alkali metal present, and sodium and potassium are preferred alkali metals, and potassium is especially preferred. These dialkali metal salts may originate from any of several sources. For instance, the initial product of the Kolbe-Schmitt synthesis of aromatic hydroxycarboxylic acids is a dialkali metal salt. A product of the Henschel synthesis of dicarboxylic acids is a dialkali metal salt. Both of these processes start with alkali metal hydroxides. Using the first process described herein, an essentially closed loop process with respect to alkali metal may be envisioned.

For instance, in the Kolbe-Schmitt synthesis of salicylic acid, the primary product is usually the disodium salt of salicylic acid. In the equations below, SA is salicylate dianion. These equations represent a first process for the complete recovery of all alkali metal (sodium) and acid (in this case sodium bisulfate) values so they may be recycled in the process.

$$Na_2SA + electrodialysis \rightarrow NaHSA + NaOH \quad (1)$$

$$NaHSA + NaHSO_4 \rightarrow H_2SA + Na_2SO_4 \quad (2)$$

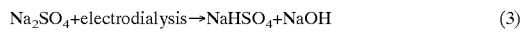

$$Na_2SO_4 + electrodialysis \rightarrow NaHSO_4 + NaOH \quad (3)$$

In the above equations, M is Na, y is 1, $R^1$ i o-phenylene, y is 1, and q is 1. Note that enough NaOH is produced in the process to be recycled back to the beginning of the Kolbe-Schmitt process, and also enough $NaHSO_4$ is regenerated to continue the process. Note that equations (1) and (2) represent the essential steps of the process described herein, while equation (3) represents an optional step which regenerates the needed alkali metal values for recycle in the overall Kolbe-Schmitt process. A first process for a monovalent anion would be as follows:

$$Na_2SA + electrodialysis \rightarrow NaHSA + NaOH \quad (4)$$

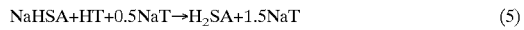

$$NaHSA + HT + 0.5NaT \rightarrow H_2SA + 1.5NaT \quad (5)$$

$$1.5NaT + electrodialysis \rightarrow 0.5NaT + NaOH \quad (6)$$

Here the major difference is that unreacted NaT is simply carried through equations (5) and (6). After electrodialysis the NaT and NaOH solutions may be recombined for use in (5). Again the sodium may be completely recycled in the overall Kolbe-Schmitt process.

Other preferred combinations of M and $R^1$ in the first process are M is potassium and $R^1$ is p-phenylene, and M is potassium and $R^1$ is 2,6-naphthylene.

The NaT or other non-reactive charge carrier which is carried through the processes of equations (5) and (6) need not be present in (5), but should be in the process stream in (6), since if not done the current efficiency in trying to convert all of the NaT in (6) to NaOH would be poor.

Similar reactions in the first process may be envisioned for other aromatic hydroxycarboxylic acids or dicarboxylic acids, other anions, and other alkali metals. Indeed, the anion may have any number of negative charges in similar schemes, just so long as the acid employed has a pKa of about 4 or less.

In the first process Y may be about 0.10 to about 1.90, preferably about 0.25 to about 1.75, is more preferably about 0.5 to about 1.5, especially preferably about 0.9 to about 1.4 and most preferably about 1. Q may be about 0.10 to about (s−0.10), preferably about 0.25 to about (s−0.25), is especially preferably about 0.5 to about (s−0.50), more preferably about 0.75 to about (s−0.75) and when s is 2, especially preferably about 1.

Suitable acids for use in the first process that have a pKa of 4 or less include $HSO_4^-$, HCl, $H_3PO_4$, $F_3CCO_2H$, and $CF_3SO_3H$. By a polyvalent anion is meant an anion that has more than one negative charge. It is preferred that X is a divalent anion and hence s is 2. It is also preferred that X is $SO_4^=$ (sulfate) anion, and it is preferred that T is chloride anion.

Electrodialysis is a well known process, see for instance B. Elvers., et al., Ed., Ullmann's Encyclopedia of Industrial Chemistry, 5th Ed., Vol. A16, VCH Verlagsgesellschaft mbH, Weinheim, 1990, p. 209–213 and 245–250, which is hereby included by reference, and electrodialysis of metal salts of inorganic acids such as $K_2SO_4$ and NaCl are especially well known. In effect, in reaction 3, and in all such reactions involving anion X, in the compound $M_qH_{s-q}X$ s is being increased at the expense of q and MOH is also being formed. In reaction 6 the ratio of HT to MT is increasing (HT is being formed) and MOH is also being formed. Thus it may be said the Bronsted acid component of the solution containing X or T is being increased. It is believed that because alkali metal hydroxide is generated in the electrolysis processes herein and organic compounds are also present, fluorinated membranes, such as Nafion® Perfluorinated Membranes (from E. I. du Pont de Nemours and Company, Wilmington, Del. U.S.A.) are particularly useful in these processes.

As the artisan will understand, a three compartment cell may be utilized in the first process which utilizes the dialkali metal salt of the aromatic hydroxycarboxylic acid or dicarboxylic acid. These starting materials are fed to the center compartment, while alkali metal hydroxide will be generated in the cathode compartment. In the anodic compartment oxygen is generated, while in the center compartment the compound $(OR^1CO_2)H_yM_{2-y}$ or $[R^2(CO_2)_2]H_yM_{2-y}$ is generated. Fresh solution of the alkali metal salt may be added to the center compartment, and solution of the center compartment removed, at such a rate so that "average" solute in the solution is $(OR^1CO_2)H_yM_{2-y}$ or $[R^2(CO_2)_2]H_yM_{2-y}$, as defined herein.

In the first process, if any of the salts of aromatic hydroxycarboxylic acid or dicarboxylic acid present in the cell has a limited solubility in water, it may be desirable to heat the cell to increase the solubility in water. Limited solubility may be encountered especially when y is greater than 1, since "free" (not being an alkali metal salt) aromatic dicarboxylic acid or aromatic hydroxy carboxylic acid will be present, and the free organic compound may have only very limited solubility in cool water. The pH of the solution in the center compartment is an indication of what the present value of y is in that compartment (see Example 1). When M is potassium and $R^1$ is p-phenylene it is preferred to carry out the process at a temperature of about 80° C. to about 105° C., especially when y is about 0.9 or more. More generally when y is about 0.9 or more it is also preferred to carry out the process at a temperature of about 80° C. to about 105° C. If the solubility of the free aromatic dicarboxylic acid or aromatic hydroxycarboxylic acid in water is relatively low, even at elevated temperatures, one may not be able to electrolyze the solution much past the point where y is about 1.

In the first process, in the electrolysis of $M_2X$ or MT, a two or three compartment cell may used, the solution of the alkali metal salt being fed to the anodic cell, or in the case of a three compartment cell, the center cell. The solution in the anodic cell may be withdrawn at such a rate that a solution of $M_qH_{2-q}X$ is withdrawn. A three compartment cell is preferable if T is a readily oxidizable anion, such as chloride. Here the solution may be withdrawn from the center compartment of a three compartment cell so that a proper mixture of HT and MT is obtained. MOH is generated in the cathodic cell of each.

The product of the second process of the invention is p-hydroxybenzoic acid, containing up to 5 mole percent of the monopotassium salt (y=1.95). Obtaining complete electrodialysis to "pure" p-hydroxybenzoic acid may require an inordinate amount of electrical energy, so it may be more economical to leave a small amount of the monopotassium salt in the PHBA and purify the free compound as by crystallization. The monopotassium salt left in solution may be recycled back to the electrodialysis for recovery.

The starting material for the second process is the corresponding mono- or dialkali metal salt of PHBA of the formula $(OR^1CO_2)H_tM_{2-t}$ wherein t is zero to about 1.5, more preferably 0 to about 0.5, especially preferably less than about 0.1, and most preferably about 0.0. This PHBA salt is then electrolyzed so that the value of t is increased to y, y normally being greater than t. Usually there will be essentially only one alkali metal present, and potassium is preferred. Using the process described herein, an essentially closed loop process with respect to alkali metal (usually potassium) may be envisioned.

In the final product of the second process it is preferred that y is about 1.97 or more.

A three compartment cell may again be utilized in the second process which utilizes an alkali metal salt of PHBA. This starting material is fed to the center compartment, while alkali metal hydroxide will be generated in the cathode compartment. In the anodic compartment oxygen is generated, while in the center compartment the compound $(OR^1CO_2)H_yM_{2-y}$ is made. Fresh solution of the PHBA alkali metal salt may be added (continuously or intermittently) to the center compartment, and solution of the center compartment removed (continuously or intermittently), at such a rate so that "average" solute in the solution is $(OR^1CO_2)H_yM_{2-y}$, as defined herein.

In the second process when y is about 1 or more the electrodialysis is carried out above about 75° C. Thus two cells can be used in series if in the starting alkali metal salt of PHBA t is about 1.0 or less. In this instance the temperature in the first cell is not critical, but in the second cell, wherein y is about 1 or more, the temperature is about 75° C. or more. Temperatures above the atmospheric boiling point of water in the solution may be used by placing the cell under elevated pressure, but the preferred upper temperature limit for this part of the electrodialysis is the boiling point of the aqueous solution at atmospheric pressure. The preferred minimum temperature is about 80° C., and it is more preferred that the minimum temperature is about 85° C.

In the second process the concentration of the alkali metal salt of PHBA in the aqueous solution that is electrodialyzed is not critical, but not so high that free PHBA will crystallize out in the three compartment cell. However, it is preferred that the concentration is high enough so that the solution will readily conduct electricity. It is also preferred that the solution concentration be relatively high so that isolation of the free PHBA after electrolysis is simplified. Isolation may be accomplished by cooling the solution and separating the crystallized PHBA. The filtrate containing some dissolved PHBA may be recycled back into the electrodialysis, i.e., "new" alkali metal salt may be dissolved in the filtrate and the solution electrodialyzed. A preferred concentration of alkali metal salt in solution is about 10 to about 35 percent by weight, more preferably about 15 to about 30 percent by weight, of free PHBA based on the total weight of water and free PHBA equivalent in the solution.

EXAMPLE 1

The electrochemical cell used was an ElectroCell AB (S-184 00 Akersberga, Sweden) "Electro MP Cell". This is was configured as a three compartment cell using Nafion® N-417 (formerly commercially available from E. I. du Pont de Nemours and Company, Wilmington, Del., U.S.A.) membranes. This membrane was a perfluorosulfonic acid polymer with an equivalent weight of 1100 reinforced with a woven perfluoropolymer fabric. The nominal thickness of the membrane was about 0.25 mm, and it had conditioned resistance of 3.5–4.0 ohms-cm$^2$. Current similar offerings of Nafion® include Nafion® N-450 and Nafion® NE-424. The effective area of each of the anode and cathode was 0.01 m$^2$. The anode was a dimensionally stable (DSA) oxygen anode, and the cathode was stainless steel.

The PHBA solution was placed in a 2 L resin kettle with a lid and clamp. The kettle was heated on a hot plate and was equipped with a magnetic stirrer, pH meter electrode, thermometer, and process inlet and outlet lines. The outlet line also had a porous thermoplastic disc filter in it. The PHBA solution was passed through a glass vacuum trap which was wrapped with electrical heater tape and acted as an auxiliary heater. The PHBA was circulated to the center compartment of the electrolysis cell.

The catholyte was 1.5 L of 1N KOH solution which was pumped from a heated reservoir to the compartment and then returned to the reservoir. The temperature of the catholyte was kept close to the PHBA solution temperature.

The anolyte was 50 mL of concentrated sulfuric acid diluted in 900 mL of distilled water. It was circulated by a pump from a reservoir through the anode compartment back to the reservoir. The anolyte had no separate heater.

A solution of the dipotassium salt of p-hydroxybenzoic acid (PHBA) was made by dissolving 120 g of PHBA and 114.6 g of KOH (pellets nominally containing 85% weight percent KOH, 15% water) in 400 mL of water. This was circulated in the center of the cell, and the solution in all three compartments were separately circulated and heated to 90° C. (during the electrolysis the catholyte was 88° C. and the center compartment solution was 83° C. at the start, and at 90°±1° C. within 25 min after the start of the electrolysis). The electrolysis was started and continued so that the voltage was varied to maintain a constant current of 15 A (ampere). During the electrodialysis water was added as necessary to replace evaporative losses.

The voltage required vs. the time elapsed for selected times during the electrolysis are shown Table 1.

TABLE 1

| Time (min) | Voltage (v) |
| --- | --- |
| 1 | 5.09 |
| 50 | 5.09 |
| 100 | 5.19 |
| 150 | 5.42 |
| 200 | 5.57 |
| 250 | 6.27 |
| 270 | 7.03 |
| 300 | 8.63 |
| 310 | 9.62 |
| 320 | 10.14 |
| 330 | 8.94 |
| 340 | 8.19 |

FIG. 1 shows the correlation of the pH of the center compartment solution with electrolysis time. It is believed that the inflection point at about 150 min represents the point at which z is approximately 1.0, or the compound present in solution is approximately the monopotassium salt of PHBA. As the time of electrolysis approaches 300 min it is believed that z is becoming quite small, so that at perhaps about 320 min the solute in the center compartment is almost pure PHBA.

Comparative Example 1

The apparatus used was similar to that in Example 1 except the PHBA solution reservoir was an open Erlenmeyer flask on a hot plate, and there was no filter or auxiliary heater in the PHBA solution lines.

A solution of the dipotassium salt of p-hydroxybenzoic acid (PHBA) was made by dissolving 120 g of PHBA and 114.6 g of KOH (pellets nominally containing 85 weight percent KOH, 15% water) in 400 mL of water. This was placed in the center compartment of the cell, and the solution in all three compartments were separately circulated. The electrolysis was started and continued so that the voltage was varied to maintain a constant current of 15 A (ampere). During the electrodialysis water was added as necessary to replace evaporative losses.

The voltages required vs. the electrolysis time elapsed for selected times during the electrolysis are shown Table 2.

TABLE 2

| Time | Voltage | Remarks |
| --- | --- | --- |
| 3 | 5.65 | |
| 70 | 5.82 | |
| 78 | 5.83 | |
| 120 | 6.43 | |
| 125 | 7.05 | |
| 130 | 8.03 | |
| 135 | 9.96 | |
| 140 | 10.7 | Gas bubbles at anode |
| 145 | 11.8 | |
| 150 | 12.2 | |
| 155 | 13.1 | |
| 160 | 13.9 | |
| 165 | 14.5 | Heat off to center compartment |
| 180 | 15.4 | Crystals forming in PHBA solution |
| 240 | 20.4 | PHBA inlet line plugged |
| 255 | 19.6 | Crystals at PHBA solution surface |
| 261 | 50.0+ | PHBA inlet line plugged |

It is clear that before complete electrolysis of the potassium salt of PHBA could be accomplished the cell required excessive voltage to operate, and in fact plugged with crystals that had formed in the PHBA (and/or its potassium salt) solution.

Figure 2:
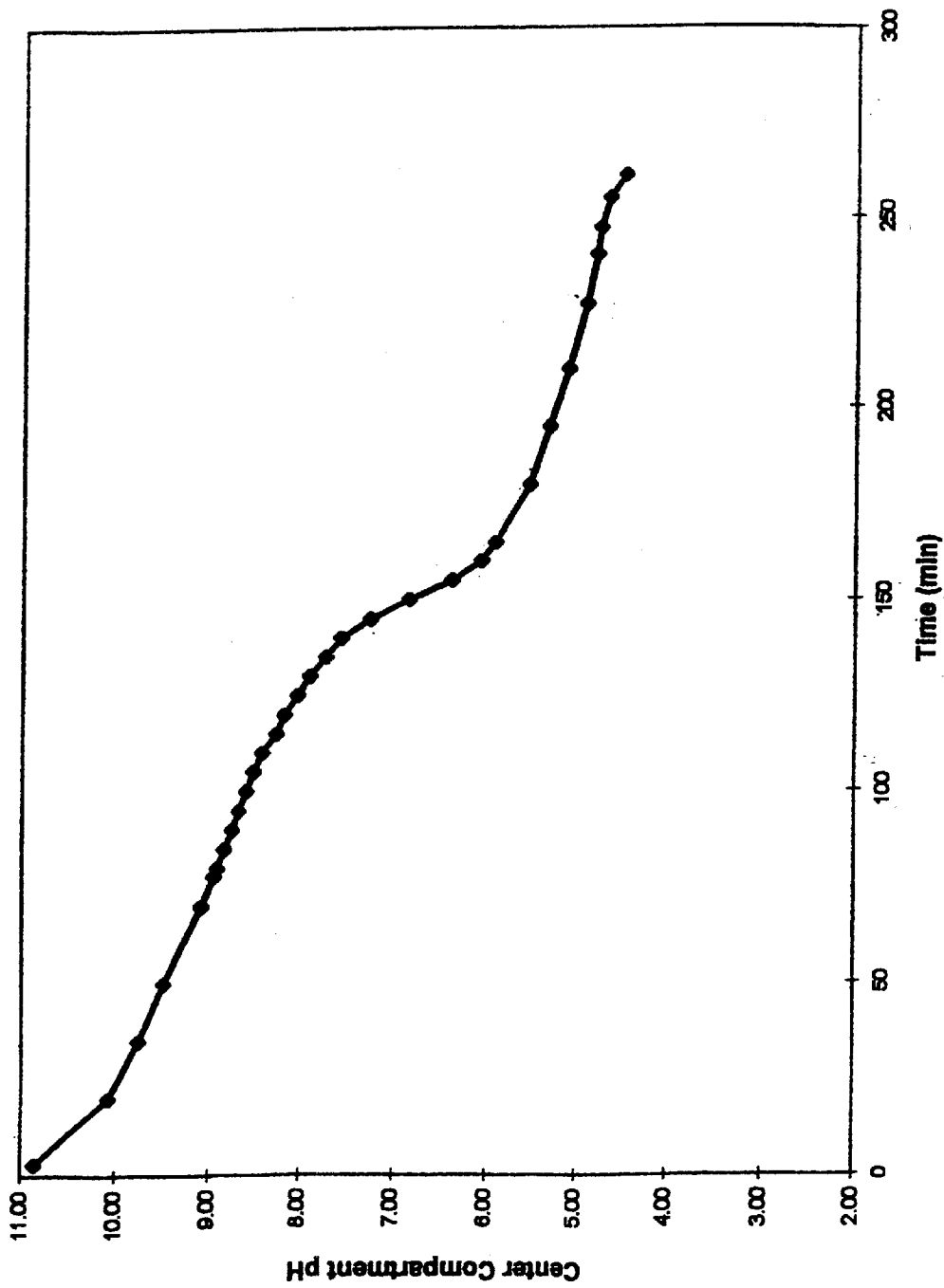
FIG. 2 is a graph showing data from Comparative Example 1 of electrolysis time vs. pH of the solution in the central compartment of the electrodialysis cell.

FIG. 2 shows the correlation of the pH of the center compartment solution with electrolysis time. It is believed that the inflection point at about 150 min represents the point at which y is approximately 1.0, or the compound present in solution is approximately the monopotassium salt of PHBA. As the time of electrolysis went over 250 min, it is believed that y was approaching 2.0.

What is claimed is:

1. A process for the preparation of p-hydroxybenzoic acid from its alkali metal salt, comprising, electrodialyzing an aqueous solution a first compound of the formula $(OR^1CO_2)H_tM_{2-t}$ to produce a second compound of the formula $(OR^1CO_2)H_yM_{2-y}$ and MOH, wherein:

$R^1$ is p-phenylene;

t is zero to about 1.50;

M is an alkali metal cation; and y is about 1.95 to 2.00;

and provided that when y or t is about 1.0 or more, said electrodialysis is carried out at a temperature of about 75° C. or more.

2. The process as recited in claim 1 wherein said alkali metal cation is potassium.

3. The process as recited in claim 2 wherein in said second compound y is 1.97 or more.

4. The process as recited in claim 2 wherein t is 0 to about 0.5.

5. The process as recited in claim 4 wherein said temperature is about 80° C. to an atmospheric boiling point of said aqueous solution.

6. The process as recited in claim 2 wherein t is about 0.0.

7. The process as recited in claim 2 wherein said temperature is about 85° C. to an atmospheric boiling point of said aqueous solution.

8. The process as recited in claim 2 wherein a concentration of free p-hydroxybenzoic acid equivalent is about 12 to about 35 percent by weight.

9. The process as recited in claim 2 wherein a concentration of free p-hydroxybenzoic acid equivalent is about 15 to about 30 percent by weight.

10. The process as recited in claim 1 wherein said temperature is about 80° C. to an atmospheric boiling point of said aqueous solution.

* * * * *